United States Patent [19]

Dines et al.

[11] Patent Number: 4,487,922
[45] Date of Patent: * Dec. 11, 1984

[54] LAYERED ORGANOPHOSPHOROUS INORGANIC POLYMERS CONTAINING CYCLIC GROUPS

[75] Inventors: Martin B. Dines, Laguna Beach; Peter M. DiGiacomo, Mission Viejo, both of Calif.

[73] Assignee: Occidental Research Corp., Irvine, Calif.

[*] Notice: The portion of the term of this patent subsequent to Mar. 17, 1998 has been disclaimed.

[21] Appl. No.: 60,077

[22] Filed: Jul. 24, 1979

[51] Int. Cl.³ .................... C08G 79/00; C08G 79/04; C08G 79/14
[52] U.S. Cl. .................. 528/395; 260/429 R; 260/429.1; 260/429.3; 260/429.5; 528/9; 528/271; 528/362; 528/374; 528/391
[58] Field of Search ............ 260/429.3, 429.5, 429 R, 260/429.1, 429.2; 528/395, 9, 362, 271, 374, 391

[56] References Cited

U.S. PATENT DOCUMENTS

| | | | |
|---|---|---|---|
| 3,231,347 | 1/1966 | Revukas | 44/69 |
| 3,491,133 | 1/1970 | Revukas | 260/429 R |
| 3,615,807 | 10/1971 | Yates | 106/288 B |
| 3,634,479 | 1/1972 | Ridenour | 260/429.7 |
| 4,256,872 | 3/1981 | DiGiacomo et al. | 528/395 |
| 4,267,308 | 5/1981 | Parziale et al. | 528/395 |
| 4,276,409 | 6/1981 | DiGiacomo et al. | 528/362 |
| 4,276,410 | 6/1981 | DiGiacomo et al. | 528/373 |
| 4,276,411 | 6/1981 | DiGiacomo et al. | 528/395 |
| 4,298,723 | 11/1981 | DiGiacomo et al. | 528/271 |
| 4,299,943 | 11/1981 | DiGiacomo et al. | 528/9 |

FOREIGN PATENT DOCUMENTS 2614356 10/1977 Fed. Rep. of Germany .
539293 9/1941 United Kingdom .

OTHER PUBLICATIONS

Chem. Abstract 83, 70750g, (1975).
Chem. Abstract 85, 13433y, (1976).
Chem. Abstract 86, 155758c, (1977).
Chem. Abstract 58, 1487b, (1963).
Chem. Abstract 55, 11161c, (1961).
Dub, "Organometallic Compounds," Springer-Verlag, Berlin VIII, pp. 187-191, (1962).
Doak et al., "Organometallic Compounds of Arsenic, Antimony and Bismuth," Wiley, Intersc., N.Y. pp. 46-49, (1970).

Primary Examiner—Helen M. S. Sneed
Attorney, Agent, or Firm—Christie, Parker & Hale

[57] ABSTRACT

Solid inorganic polymers are derivatives of phosphorous or phosphonic acids which contain cyclic organo groups selected from the group consisting of alicyclics, aromatics and heterocyclics. They are characterized by the structural linkage of three oxygens bonded to phosphorus to one or more tetravalent metals selected from the group consisting of titanium, zirconium, cerium, hafnium, lead, thorium and uranium. The molar ratio of phosphorus to tetravalent metal is about 2 to 1. One use for the polymers is as stationary phases or supports in chromatography.

14 Claims, 8 Drawing Figures

LAYERED ORGANOPHOSPHOROUS INORGANIC POLYMERS CONTAINING CYCLIC GROUPS

CROSS-REFERENCE TO RELATED APPLICATIONS

This application is related to the following copending applications: Ser. No. 945,971 filed Sept. 26, 1978, now U.S. Pat. No. 4,232,146 issued Nov. 4, 1980, Ser. No. 952,228 filed Oct. 17, 1978, now U.S. Pat. No. 4,235,990 issued Nov. 25, 1980, Ser. No. 966,197 filed Dec. 4, 1978, now U.S. Pat. No. 4,235,991 issued Nov. 25, 1980, Ser. No. 7,275 filed Jan. 29, 1979, Ser. No. 43,810 filed May 30, 1979 and titled Process for Preparing Layered Organophosphorus Inorganic Polymers, Ser. Nos. 54,107 and 54,097 filed July 2, 1979 and titled, respectively, Layered Cyano End Terminated Organophosphorus Inorganic Polymers and Layered Organophosphorous Inorganic Polymers Containing Mercapto or Thio Groups, and four applications filed concurrently herewith, and titled: Layered Organophosphorus Inorganic Polymers Containing Acyclic Groups, Ser. No. 60,079 Layered Organoarsenous Inorganic Polymers, Ser. No. 60,078 Layered Organophosphorus Inorganic Polymers Containing Mixed Functional Groups, Ser. No. 60,250 and Layered Organophosphorus Inorganic Polymers Containing Oxygen Bonded to Carbon Ser. No. 60,249. The entire disclosure of each of these applications is hereby incorporated herein by this reference.

BACKGROUND OF THE INVENTION

The present invention is directed to solid inorganic polymers having organo groups anchored to the surfaces of the polymers. The majority of the polymers formed are layered crystals which display intercalation activity.

The interface surfaces of solids are responsive regions of chemical and physical action. In many practical chemical and physical phenomena such as absorption, corrosion, inhibition, heterogeneous catalysis, lubrication, ion exchange activity, adhesion and wetting, and electrochemistry, activity occurs as a consequence of the presence of a definable solid surface. Solid agents are preferred in most processes over solution or homogeneously dispersed reactive alternatives primarily because they greatly simplify efficient separation of products from reactants. However, solids invariably suffer from deficiencies in activity and selectivity in the conversions they effect, due to inherent heterogeneity in their active sites which arises from the nature of their surface structure. Furthermore, much of the active sites are usually buried within the surface, and as a result of these two factors, elevated temperature and low conversions are typically encountered. Exceptions in which homogeneous catalysts are employed have been the Monsanto process for the production of acetic acid from methanol and carbon monoxide employing rhodium, the production of linear alcohols from olefins and syngas, ethylene oxidation by the Wacker process, catalysis of olefins to form polymers, and other polymerization systems.

In an effort to achieve the best features of both homogeneous and heterogeneous processes, efforts have been made to chemically "anchor" known effective solution agents such as phosphines, nitriles, cyclopentadiene and the like, onto certain solids. Porous inorganic surfaces and insoluble organic polymers have been employed. Silica has been the inorganic of choice, the bonded ligand being attached by reaction with the —OH groups projecting from the surface. The organic polymer most used has been polystyrene, with an appropriate metal-coordinating function bonded via the phenyl rings. Results have been generally encouraging. However, there have been pervasive problems deriving from the non-uniform situation of sites which has manifested itself in loss of expected selectivity, activity and even in attrition.

Efforts at heterogenizing catalysts have been discussed by Bailar, "Heterogenizing Homogeneous Catalysts," Catalysis Reviews—Sci. & Eng. 10(1) 17–35 (1974) and Hartley and Vezey, "Supported Transition Metal Complexes as Catalysts," Advances in Organometallic Chemistry 15, 189–235(1977). The entire disclosure of which is incorporated herein.

Many inorganic solids crystallize with a layered structure and some could present sites for anchoring active groups. In this form, sheets or slabs with a thickness of from one to more than seven atomic diameters lie upon one another. With reference to FIG. 1, strong ionic or covalent bonds characterize the intrasheet structure, while relatively weak van der Waals or hydrogen bonding occurs between the interlamellar basal surfaces, in the direction perpendicular to their planes. Some of the better known examples are prototypal graphite, most clay minerals, and many metal halides and sulfides. A useful characteristic of such materials is the tendency to incorporate "guest" species in between the lamella.

In this process, designated "interclalation", the incoming guest molecules, as illustrated in FIG. 2, cleave the layers apart and occupy the region between them. The layers are left virtually intact, since the crystals simply swell in one dimension, i.e., perpendicular to the layers. If the tendency to intercalate is great, then the host layered crystal can be thought of as possessing an internal "super surface" in addition to its apparent surface. In fact, this potential surface will be greater than the actual surface by a factor of the number of lamella composing the crystal. This value is typically on the order of $10^2$–$10^4$. Although edge surface is practically insignificant compared to basal surface, it is critical in the rate of intercalation, since the inclusion process always occurs via the edges. This is because bonding within the sheets is strong, and therefore, basal penetration of the sheets in an unlikely route into the crystal.

Previous studies of the intercalative behavior of layered compounds have mainly been conducted by solid-state chemists interested in the bulk effects on the layered host materials. Graphite has, for example, been extensively studied from an electronic point of view. In general, the function of the host is essentially passive. That is, on intercalation the host serves as the matrix or surface with which the incoming guest molecules interact, but throughout the process on deintercalation the guests undergo only minor perturbation.

In order for a more active process to occur during intercalation, such as selective complexation or catalytic conversion, specific groups must be present which effect such activity. There might also be some preferable geometric environment about each site, as well as some optimal site-site spacing. These considerations have not been extensively applied to intercalation chemistry simply because such kinds of active groups required are not found on layered surfaces.

An approach in which catalytically active agents have been intercalated into graphite or clays for subsequent conversions has been described in "Advanced Materials in Catalysis", Boersma, Academic Press, N.Y. (1977), Burton et al, editors, and "Catalysis in Organic Chemistry", Pinnavia, Academic Press, N.Y. (1977), G. V. Smith, editor, each incorporated herein by reference. In neither case could it be shown that any activity was occurring within the bulk of the solid. Rather, it is believed that edge sites are responsible for the reactivity observed. In none of the cases was the active site covalently anchored, or fixed upon the lamella of the host. Instead, the normal ion or van der Waals forces of intercalated guests were operating.

One of the few layered compounds which have potential available sites is zirconium phosphate $Zr(O_3POH)_2$. It exists in both amorphous and crystalline forms which are known to be layered. In the layered structure, the site-site placement on the internal surfaces is about 5.3 Å, which leads to an estimated 25 Å$^2$ area per site. This area can accommodate most of the functional groups desired to be attached to each site. The accepted structure, symbolized projection of a portion of a layer of this inorganic polymer and a representation of an edge view of two layes, are shown respectively in FIGS. 3, 4 and 5.

Besides the advantageous structural features of zirconium phosphate, the material is chemically and thermally stable, and non-toxic.

Quite a bit of work has been conducted on the zirconium phosphate, mainly because it has been found to be promising inorganic cation exchanger for alkali, ammonium and actinide ions, Alberti, "Accounts of Chem. Research", 11, 163 (1978), incorporated herein by reference. In addition, some limited work has been described on the reversible intercalation behavior of layered zirconium phosphate toward alcohols, acetone, dimethylformamide and amines, Yamaka and Koizuma, "Clay and Clay Minerals" 23, 477 (1975) and Michel and Weiss, "Z. Natur," 20, 1307 (1965) both incorporated herein by reference. S. Yamaka described the reaction of this solid with ethylene oxide, which does not simply incorporate between the layers as do the other organics, but rather was found to irreversibly react with the acidic hydroxyls to form a covalently bonded product, Yamaka, "Inorg. Chem." 15, 2811, (1976). This product is composed of a bilayer of anchored ethanolic groups aimed into interlayers. The initial layer-layer repeat distance is expanded from about 7.5 Å to 15 Å, consistent with the double layer of organics present. The overall consequence of this reaction is to convert inorganic acid hydroxyls to bound inorganic alkanol groups. This conversion, while of interest, has limited if any improvement over the hydroxyls already available on zirconium phosphate.

A very recently reported effort in the field is Alberti, et al., "J. Inorg. Nucl. Chem.", 40, 1113 (1978) which is incorporated herein by reference. A method similar to that of this invention for the preparation of zirconium bis(benzenephosphonate), zirconium bis(hydroxymethanephosphonate) monohydrate, and zirconium bis(monoethylphosphate) is described, with descriptions of the properties for these products.

Following the Alberti publication, a paper by Maya appeared in "Inorg. Nucl. Chem. Letters", 15, 207 (1979), describing the preparation, properties and utility as solid phases in reversed phase liquid chromatography for the compounds $Zr(O_3POC_4H_9)_2 \cdot H_2O$, $Zr(O_3POC_{12}H_{25})_2$ and $Zr(O_3POC_{14}H_{21})_2$. All of the compositions that are described herein can be useful in gas phase, liquid phase, gas liquid, reversed phase, and bulk and thin layer chromatography. The compounds can also be useful as hosts and carriers for organic molecules and especially biologically active organic molecules (e.g. methoprene).

SUMMARY OF THE INVENTION

According to the present invention there is provided solid inorganic polymers having organo groups covalently bonded to phosphorus atoms and in which the phosphorus atoms are, in turn, covalently bonded by oxygen linkage to tetravalent metal atoms and, when formed in a layered crystalline state, provide the organo groups on all of the apparent and interlamellar surfaces.

More particularly, the invention relates to solid inorganic polymers containing cyclic organo groups, selected from the group comprising alicyclics, aromatics and heterocyclics. The process of preparation comprises a liquid medium reaction in which at least one organophosphorus acid compound of the formula:

$$[(HO)_2OP]_nR$$

wherein n is 1 or 2 and R is an organo group covalently coupled to the phosphorus atom, and wherein when n is 2, R contains at least three carbon atoms and is directly or indirectly coupled to phosphorus atoms through different carbon atoms whereby the two phosphorus atoms are separated by at least two carbon atoms, is reacted with at least one tetravalent metal ion preferably selected from the group consisting of zirconium, cerium, thorium, uranium, lead, hafnium and titanium. The molar ratio of phosphorus to the tetravalent metal is 2 to 1. Reaction preferably occurs in the presence of an excess of the organophosphorus acid compound and the metal ion is provided as a compound soluble in the liquid medium.

Where only one specie of an organophosphorus acid compound is provided as the reactant with the tetravalent metal compound, the end product will have the empirical formula $M(O_3PR)_2$. Phosphoric and/or phosphorous acid can also be present as reactive diluents to form part of the solid inorganic polymeric structure which is the product of the reaction.

The products formed are layered crystalline to amorphous in nature. For all products, the R groups may be directly useful or serve as intermediates for the addition or substitution of other functional groups. When the product is crystalline and n is 2, cross-linking between the interlamellar layers occurs.

The normal liquid medium is water. However, organic solvents, particularly ethanol, may be employed where water will interfere with the desired reaction. Preferably, the solvent is the solvent in which the organophosphorus acid compound is prepared. Where the organophosphorus acid compound has a sufficiently low melting point, it can serve as the liquid media.

The metathesis reaction occurs at temperatures up to the boiling point of the liquid medium at the pressures involved, typically from ambient to about 150° C. more preferably from ambient to about 100° C. While formation of the solid inorganic polymer is almost instantaneous, the degree of crystallinity of the product can be increased by refluxing the reaction products for times from about 5 to 15 hours. Crystallinity is also improved by employing a sequestering agent for the tetravalent metal ion.

THE DRAWINGS

Figure 1:
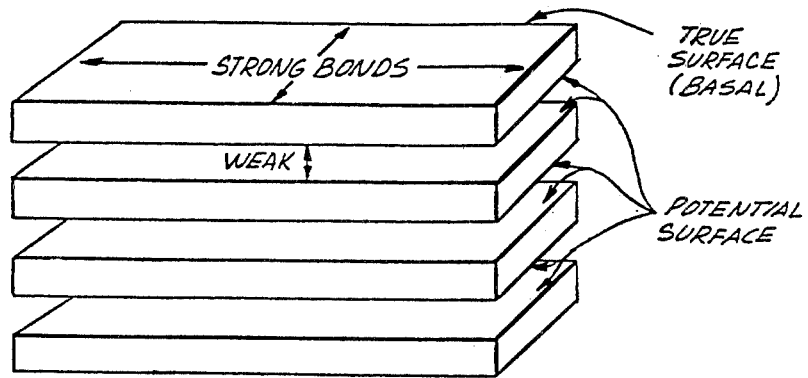
FIG. 1 illustrates a layered microcrystal. Each lamellar slab is formed of strong covalent bonds and has a thickness of about 10 atoms.
Figure 2:
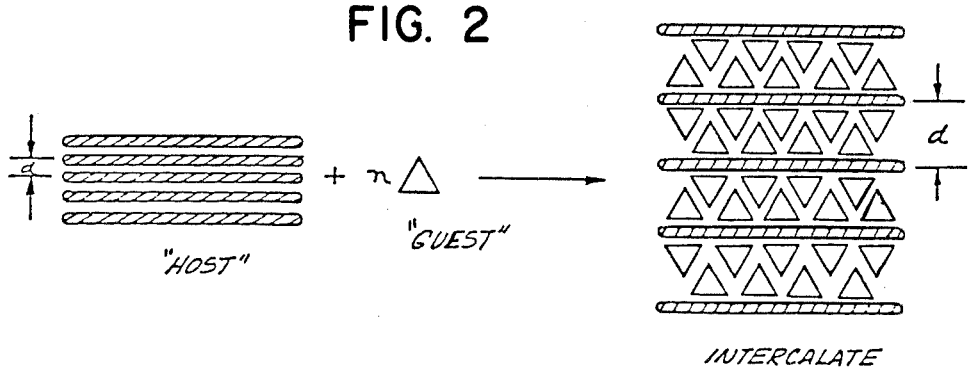
FIG. 2 illustrates intercalation where the interlayer distance is shown as "d."
Figure 3:
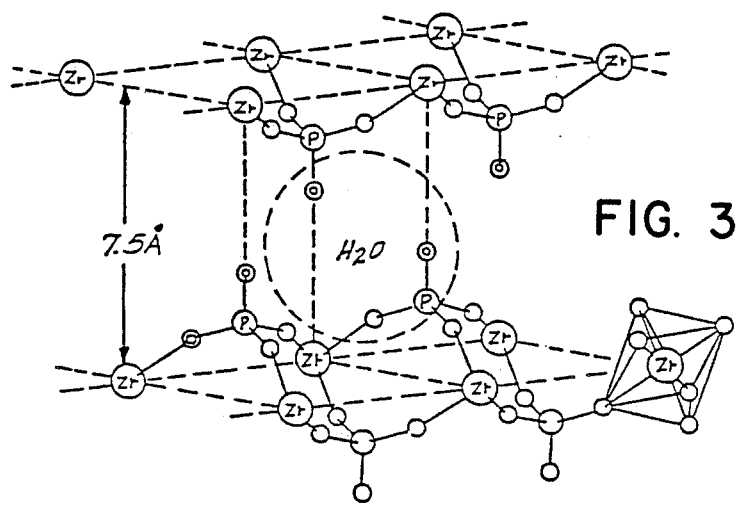

FIG. 3 illustrates the accepted structure for zirconium phosphate and spacing between layers. The dashed lines between zirconium (Zr) atoms is to establish the plane between them. In the drawing P=phosphorus, O=oxygen and water of hydration is shown.

Figure 4:
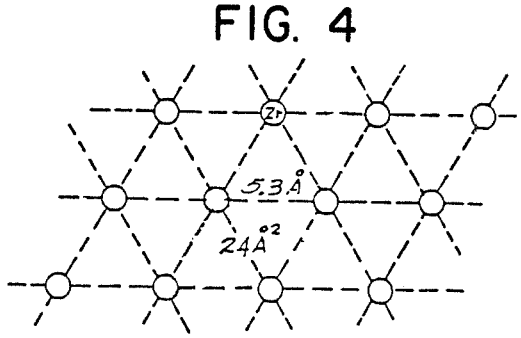

FIG. 4 illustrates a projection of zirconium plane showing accepted spacing between Zr atoms and the available linkage area.

Figure 5:
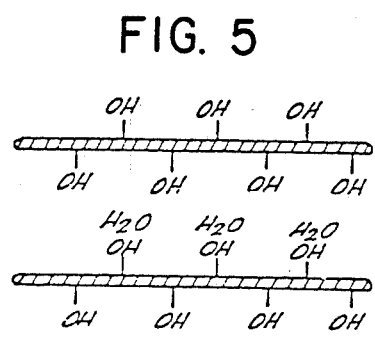

FIG. 5 is a symbolized depiction of spaced zirconium phosphate layers showing covalently bonded hydroxyl groups and water of hydration.

Figure 6:
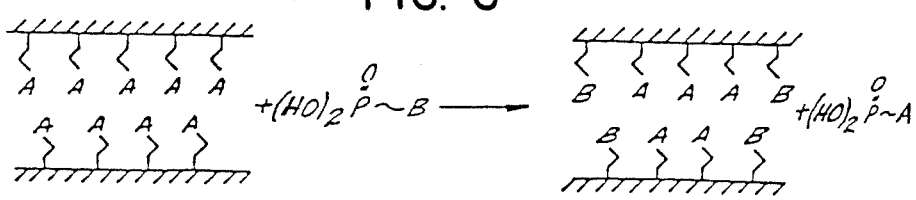

FIG. 6 illustrates an exchange reaction between anchored groups "A" and groups to be substituted for "B", and 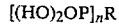 represents the portion of the organo group linking the terminal group "A" or "B" to the crystals or the organophosphorus acid compound reactant.

Figure 7:
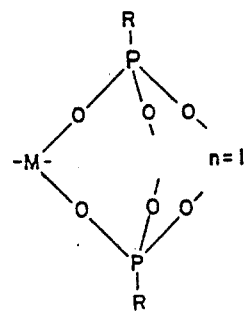

FIG. 7 shows the basic structural unit of the inorganic polymer formed by the process of the invention where n is 1 and where P=phosphorus atom, O=oxygen atom, M=tetravalent metal atom and R is the organo group.

Figure 8:
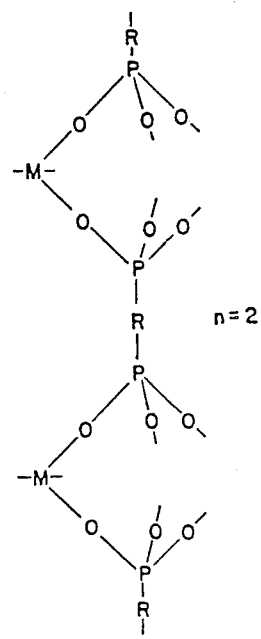

FIG. 8 shows the basic structural unit of the inorganic polymer formed by the Process of the invention where n is 2 and where P=phosphorus atom, O=oxygen atom, M=tetravalent metal atom and R is the organo group.

DETAILED DESCRIPTION

According to the present invention there is provided solid inorganic polymers in layered crystalline to amorphous state by the liquid phase metathesis reaction of at least one organophosphorus acid compound having the formula:

[(HO)₂OP]ₙR wherein n is 1 or 2 and R is a cyclic organo group selected from the group consisting of alicyclics, aromatics and heterocyclics, covalently coupled to the phosphorus atom, with at least one tetravalent metal ion selected from the group consisting of zirconium, thorium, cerium, uranium, lead, hafnium and titanium to form a solid inorganic polymer precipitate in which phosphorus is linked to the metal by oxygen and the group is covalently bonded to the phosphorus atom. Where, in the organophosphorus compound, n is 2, the end product occurs in the bis configuration. In this configuration, R must contain three or more carbon atoms, preferably from two to about twenty-six carbon atoms, such that at least two carbon atoms separate the phosphorus atoms. In this bis configuration no single carbon atom is bound directly or indirectly to more than one [PO(OH)₂] group. When n is 1, and as depicted in FIG. 7, the organo groups will be pendant from phosphorus atoms. When n is 2, and as depicted in FIG. 8, cross-linking will occur between interlamellar surfaces of the crystalline end product. Typically, the tetravalent metal ion is provided as a soluble salt MX wherein M is as defind above and X is the anion(s) of the salt. The typical anions include halides, $HSO_4^{-1}$, $SO_4^{-2}$, $O_2C-CH_3^{-1}$, $NO_3^{-1}$, $O^{-2}$ and the like.

The majority of the polymeric reaction products formed are found to be layered crystalline or semi-crystalline in nature and, as such, provide layered structures similar to zirconium phosphates. The remainder are amorphous polymers possessing a large quantity of available pendant groups By the term "organophosphorus acid compound", as used herein, there is meant a compound of the formula:

[(HO)₂OP]ₙR wherein n is 1 or 2, R is any group which will replace a hydroxyl of phosphoric acid and/or the hydrogen of phosphorous acid and couple to the acid by a covalent bond. Coupling to the acid may be through carbon, oxygen, silicon, sulfur, nitrogen and the like. Coupling through carbon or an oxygen-carbon group is presently preferred.

When, in the organophosphorus compound, n is 2, the end product occurs in the bis configuration. In this configuration, R must contain three or more carbon atoms, preferably from two to about twenty-six carbon atoms, such that at least two carbon atoms separate the phosphorus atoms. In this bis configuration, no single carbon atom is bound directly or indirectly to more than one [PO(OH)₂] group. Thus the groups which link to the metal have the basic structural formula:

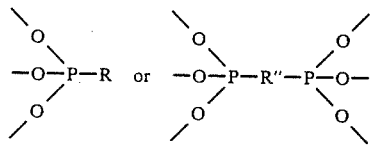

wherein R" is a bis group containing at least two carbon atoms bonded directly or indirectly to phosphorus and such that no phosphorus atoms are boned directly or indirectly to the same carbon atom. The basic structures of the inorganic polymer forms are shown in FIGS. 7 and 8.

When coupling is through carbon, the organo phosphorus acid compound is an organo phosphonic acid and the product a phosphonate. When coupling is through oxygen-carbon, the organophosphorus acid compound is an organo-phosphoric monoester acid and the product a phosphate.

The general reaction for phosphonic acids alone is shown in equation (1) below and for monoesters of phosphoric acid alone by equation (2).

$$M^{+4} + 2(HO)_2OPR \longrightarrow M(O_3P-R)_2 + 4H^+ \quad (1)$$

$$M^{+4} + 2(HO)_2OP-OR' \longrightarrow M(O_3P-OR')_2 + 4H^+ \quad (2)$$

wherein R' is the remainder of the organo group.

The product contains phosphorus to metal in a molar ratio of about 2 to 1, and the empirical formula for the product would show all organo groups bound to phosphorus.

While nowise limiting, the R groups attachable to phosphorus may be saturated and unsaturated, substituted and unsubstituted and include, among others, alkylene, alkyloxy, alkyne, aryl, haloalykl, alkylaryl, aryloxy, mercaptoalkyl, aminoalkyl, carboxyalkyl, morpholinoalkyl, sulfoalkyl, phenoxyalkyl, beta-diketo alkyl, cyanoalkyl, cyanoalkoxy, heterocyclics and the like.

In general, the organo group should occupy no more than about 25 Å$^2$ for proper spacing. This limitation is imposed by the basic crystal structure of zirconium phosphate. Referring to FIG. 4, a spacing of 5.3 Å is shown between zirconium atoms in the zirconium plane of a crystal a total area of about 24 Å$^2$ is shown for the space bounded by zirconium atoms. It follows that any group anchored on each available site cannot have an area much larger than the site area and maintain the layered structure.

This limitation can be avoided through the use of a combination of larger and smaller groups, i.e., mixed components. If some of the sites are occupied by groups which have an area much less than about 24 Å$^2$, adjacent groups may be somewhat larger than 24 Å$^2$ and still maintain the layered structure of the compound.

The cross-sectional area which will be occupied by a given organo group can be estimated in advance of actual compound preparation by use of CPK space filling molecular models (Ealing Company) as follows: A model of the alkyl or aryl chain and terminal group is constructed, and it is situated on a scaled pattern of a hexagonal array with 5.3 Å site distances. The area of the group is the projection area on this plane. Some areas which have been determined by this procedure are listed in Table 1.

TABLE I

| Moiety | Minimum Area (Å$^2$) | Moiety | Minimum Area (Å$^2$) |
| --- | --- | --- | --- |
| Alkyl chain | 15 | Isopropyl | 22.5 |
| Phenyl | 18 | t-butyl | 25 |
| Carboxyl | 15 | Chloromethyl | 14 |
| Sulfonate | 24 | Bromoethyl | 17 |
| Nitrile | 9 | Diphenylphosphine | 50 (approx.) |
| Morpholinomethyl | 21 | Mercaptoethyl | 13.5 |
| Trimethylamino | 25 | | |

The process for the formation of the novel inorganic polymers is a metathesis reaction conducted in the presence of a liquid medium receptive to the tetravalent metal ion at a temperature up to the boiling point of the liquid medium, preferably from ambient to about 150° C. and, more preferably, to about 100° C. at the pressure employed.

While water is the preferred liquid medium, as most of the organophosphorus acid compounds are water soluble, an organic solvent such as ethanol may be employed, where water interferes with the reaction. There need only to be provided a solvent for the organophosphorus acid compound since the tetravalent ion can be dispersed as a solid in the solvent for slow release of the metal ion for reaction with the organophosphorus acid compound. It if has a sufficiently low melting point, the organophosphorus acid compound may serve as a solvent. Typically, the liquid medium is the liquid medium in which the organophosphorus acid is formed.

For complete consumption of the tetravalent compound, the amount of acid employed should be sufficient to provide two moles of phosphorus per mole of tetravalent metal. An excess is preferred. Phosphorous acid and/or phosphoric acid, if present, will enter into the reaction and provide an inorganic polymer diluted in respect to the organo group in proportion to the amount of phosphorous or phosphoric acid employed.

Reaction is virtually instantaneous at all temperatures leading to precipitation of layered crystalline, semi-crystalline or amorphous inorganic polymer solid.

The amorphous phase appears as a gel similar to silica gel. The gel can be crystallized by extended reflux in the reaction medium, usually from about 5 to about 15 hours. The semi-crystalline product is characterized by a rather broad X-ray powder diffraction pattern.

The presence of sequestering agents for the metal ion slows down the reaction and also leads to more highly crystalline products. For instance, a semi-crystalline solid has been prepared by the aqueous phase reaction of zirconium oxy-chloride and excess 2-carboxyethyl phosphonic acid, followed by 15 hours of reflux. A highly crystalline modification was prepared under identical conditions except that hydrogen fluoride was added to the reaction mixture. A slow purge of $N_2$ over the surface of the reaction solution slowly removed the fluoride from the system. Fluoride is a very strong complexing agent for zirconium ions. The slow removal of fluoride results in slow release of the metal ion for reaction with the phosphonic acid, resulting in an increase in crystallinity.

A similar enhancement of crystallinity was obtained in the reaction of thorium nitrate with 2-carboxyethyl phosphonic acid. Nitrate ion is a sequestering agent for thorium and the rate of formation of this product is slow and the product polymer quite crystalline.

As compared to zirconium phosphate forming crystals of 1–5 microns, crystals of 100 to greater than 1000 micron in size have been prepared in accordance with the invention.

A property critical for many of the likely uses of the products is their thermal stability. This is because deficiencies in activity can be compensated for by reasonable increases in operating temperature. A standard method for thermal characterization is thermal gravimetric/differential thermal analysis (TGA/DTA). These techniques indicate changes in weight and heat flow of substances as a function of temperature. Thus, decomposition and phase changes can be monitored as temperature increases.

Zirconium phosphate itself is quite a stable material. Interlayer water is lost at about 100° C., and a second dehydration involving the phosphates occurs above 400° C. The practical ion-exchanging abilities are lost in this step.

The inorganic polymers of this invention are also stabilized toward thermal decomposition as compared to pure organic analogs as a result of the fixation and separating effect of the inorganic support.

For zirconium chloromethyl phosphonate, for instance, weight loss did not commence until well above 400° C. The organic fragment was half lost at about 525° C., indicating remarkable stability. Decomposition of zirconium 2-carboxyethylphosphonate begins between 300° and 400° C. The decomposition process inflection point, approximate mid-point, falls at about 400° C.

While not bound by theory, phosphates probably decompose like carboxylic esters to yield acid and unsaturates, whereas phosphonates likely form radicals by homolytic cleavage. Both nitrophenyl and cyanoethyl phosphates of zirconium decompose at about 300° C. The phenylphosphonate decomposes at about 425° C.

Besides proving the suitability of such compounds in elevated temperature applications, the TGA analysis affirmed covalent bonding to phosphorus. This is because normal intercalative interactions are reversed within 10° to 100° C. above the boiling point of the guest.

The process disclosed herein permits a wide variety of inorganic polymers to be formed having the characteristic of the organo group protected by the inorganic polymer structure and, with subsequent exchange or substitution reactions, the formation of other inorganic polymers. Polymers formed may be block, random and the like.

For instance, a mixture of phenyl phosphonic acid and phosphorous acid was simultaneously reacted with zirconium ion to yield a single solid phase. The interlamellar distance was the same as zirconium phenyl phosphonate, or about 15.7 Å. There was no reflection at 5.6 Å, the normal spacing for zirconium phosphite. This established that the largest group should determine interlamellar distance and indicated that a discreet zirconium phosphite phase was not present. Evidence of a change in chemical environment of P-H band was established by infrared analysis. In infrared analysis of zirconium phosphite, P-H stretching is observed as a sharp band at 2470 cm$^{-1}$ (moderate intensity). In the mixed compound solid, this band was shifted to 2440 cm$^{-1}$ and broadened.

Another route is to exchange one pendant group for another. While not bound by theory, the present expected points of exchange are at the periphery of the crystal and are schematically illustrated in FIG. 6. Such bifunctional materials exhibit the quality of providing terminal groups for attracting species for intercalation and then interaction with the internal groups.

The reaction of bis acids with tetravalent metal ions permits interlamellar cross-linking by a reaction such as (HO)$_2$OPCH$_2$CH$_2$OP(OH)$_2$+M$^{+4}$→ ≣-CH$_2$CH$_2$-≣ where as in FIG. 6, ⊔⊔⊔⊔ represents the interlamellar layer to which the alkyl group is anchored. As with all organo groups, for the bias configuration at least two carbon atoms are present, preferably from two to twenty atoms, and the phosphorus atoms are linked directly or indirectly to different carbon atoms. Since size of the linking group will control and fix interlamellar spacing, there is provided effective laminar sieves of fixed spacing for application analogous to that of molecular sieves.

Ion exchange activity as been established with pendant carboxylic acid groups. Prepared zirconium 2-carboxyethyl phosphonate was established to have an interlayer distance of 12.8 Å. When intercalated to form its n-hexylammonium salt interlayer distance increased to 27.2 Å. When sodium was taken up, layer spacing increased to 14.2 Å. X-ray and infrared data indicated the highly crystalline inorganic polymer to behave as expected for carboxylic acid with behavior analogous to ion exchange resins except that both external and interal surfaces were functional establishing them as super surface ion exchange resins. Moreover, since the inorganic polymers can be prepared as microcrystalline powders, diffusion distances are short.

As summarized in Table 1, nitrile and mercapto anchored groups show the ability to take up silver and copper ions at room temperature for catalytic activity.

TABLE II

| Anchored Group | Metal Ion | Loading $\frac{\text{mMole Metal}}{\text{mMole Zr}}$ |
|---|---|---|
| —O~CN | 0.1 M Ag$^+$ | 0.20 |
| ~SH | 0.1 M Ag$^+$ | 1.00 |
| —O~CN | 0.1 M Cu$^{++}$ | 0.10 |
| —O~CN | 0.1 M Cu$^{++}$ 0.5 M HOAc 0.5 M NaOAc | 0.10 |

~ = groups formed of carbon and hydrogen.
OAc = acetate radical.

The alternate to catalytic utility is to attach the metals to the organophosphorus acid prior to reaction with the soluble tetravalent metal compound.

The high surface area of the crystalline products also make them utile for sorption of impurities from aqueous and non-aqueous media.

Another utility is as an additive to the polymeric compositions. Similar to the high aspect ratio provided by solids such as mica which improve the stress strain properties of the polymers, the powdered inorganic polymer products of the invention can serve the same function and add features. By the presence of reactive end groups on the bonded organo groups, chemical grafting to the polymer network can be achieved to increase composite crystallinity and elevating heat distortion temperature. In addition, the presence of phosphorus induces flame retardant properties, as would bound halogen.

Still other utilities include solid lubricants which behave like mica, graphite and molybdenum disulfide; solid slow release agents where intercalated materials can be slowly leached or released from the internal layers of the crystals, substances displaying electrical, optical, phase or field changes with or without doping and the like.

While nowise limiting, the following Examples are illustrative of the preparation of solid inorganic polymers of this invention and some of their utilities.

In the Examples conducted in the atmosphere no extraordinary precautions were taken concerning oxygen or moisture. Reagents were usually used as received from suppliers. The products formed are insoluble in normal solvents and do not sublime. However, the combined weight of yield data, spectroscopy, elemental analysis and powder diffraction results confirm the compositions reported with good reliability.

EXAMPLE I

Preparation of:

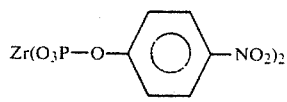

To a suitable reaction vessel is added 1.696 g of a 37% solution of hydrochloric acid and 3.155 g of 3.155 g

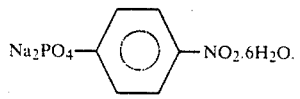

Upon combining the hydrochloric acid and the salt there is produced the acid

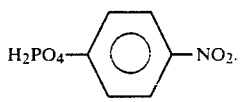

The paranitrophenyl phosphoric acid produced by the above reaction was reacted with 1.321 g of $ZrOCl_2 \cdot 8H_2O$ in about 50 ml of water. A precipitate formed almost immediately upon the addition of the $ZrOCl_2 \cdot 8H_2O$.

The resulting precipitate and supernatant liquid was heated to about 90° C. for a period of about two and one-half days (about 60 to 72 hours). The precipitate formed was

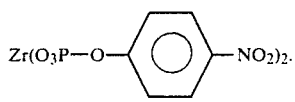

The

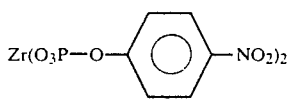

was filtered and washed with water. The precipitate was washed following the water wash with subsequent washes of acetone and ether. The acetone and ether washes filtered much easier than the water wash. The resulting separated precipitate was dried in an oven at 55° C. which after drying weighed about 1.656 g.

Elemental analysis of the recovered product provided the following results: 15.48% C; 2.25% H; and 2.09% N. An X-ray powder diffraction pattern showed the compound to be semicrystalline having an interlayer spacing of 15.8 Å.

EXAMPLE II

Preparation of:

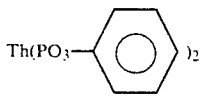

In a suitable reaction vessel containing 150 ml of water was added 2.028 g of

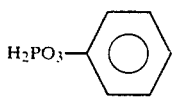

and 3.477 g of $Th(NO_3)_4 \cdot 4H_2O$. Also added to the reaction vessel was one ml of a 38 percent solution of hydrochloric acid.

Upon adding the reactants a precipitate formed almost immediately. The resultant mixture was heated overnight (about 12 hours) to promote layering within the mixture. The solid produced exhibited hydrophobic properties.

The mixture was filtered to separate the solid precipitate from the supernatant liquid. The precipitate

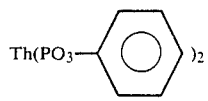

was washed with water and dried at a temperature of about 75° C. for three hours. The weight of the precipitate following drying was about 3.442 g.

An X-ray powder diffraction pattern showed the compound to be crystalline having an interlayer spacing of 14.7 Å.

EXAMPLE III

Preparation of:

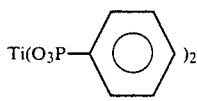

In a suitable reaction vessel containing 100 ml of water was added 5.665 g of

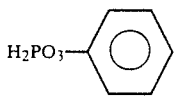

and 8.087 g of a 30 percent by weight aqueous solution of $TiOCl_2$ and 1 ml of 38 percent hydrochloric acid.

Upon mixing the reagents a precipitate appeared almost immediately upon mixing. The mixture containing the reactants was refluxed overnight under reflux conditions. Following refluxing the resultant mixture was filtered and the precipitate separated and washed with water. The precipitate was then dried in an oven at about 50° C. for a few hours until a constant weight was obtained. The final weight of the precipitate,

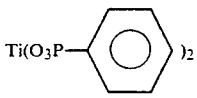

was 5.722 g. The theoretical yield was 6.480 grams which provided an 88.3 percent yield for the reaction.

An X-ray powder diffraction pattern showed the compound to be crystalline having an interlayer spacing of 15.2 Å.

EXAMPLE IV

Preparation of:

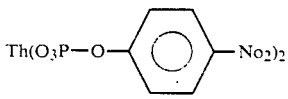

To a reaction vessel was added 3.032 g of

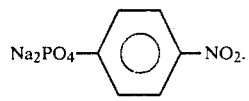

The sodium salt was neutralized with 2.05 g of a 38 percent hydrochloric acid to produce the acid,

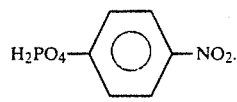

The resulting mixture was diluted to about 100 ml with water. To the aqueous solution was added 2.209 g of $Th(NO_3)_4 \cdot 4H_2O$. The

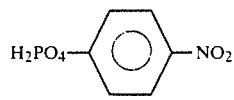

was present in a slight stoichiometric excess over the $Th(NO_3)_4 \cdot 4H_2O$.

A precipitate of

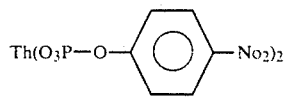

appeared almost immediately upon mixing the reactants. The mixture was heated overnight. The resultant mixture was filtered to separate the solid precipitate from the supernatant liquid. The precipitate was washed with successive washes of water, acetone and ether. The precipitate was then dried at a temperature of about 55° C. The dried solid precipitate weighed about 2.763 g.

Elemental analysis of the recovered product provided the following results: 18.54% C; 2.11% H; and 2.56% N. An X-ray powder diffraction pattern showed the compound to be semicrystalline having an interlayer spacing of 16.4 Å.

EXAMPLE V

Preparation of:

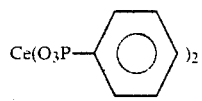

In a reaction vessel was added $H_4Ce(SO_4)_4$ and water in an amount sufficient to dissolve the $H_4Ce(SO_4)_4$. The $H_4Ce(SO_4)_4$ decomposes slowly so no attempt was made to quantitatively measure the amount dissolved in the water. The resultant solution was filtered twice to remove any undissolved solids. The salt appeared to stabilize in the aqueous solution following the initial quick decomposition experienced upon first solvation. The filtered solution had a bright yellow color.

The resultant solution was mixed with an excess of

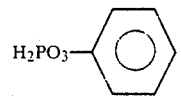

and the mixture was heated. A solid precipitate formed which exhibited greater crystalline characteristics after heating the solution for about two hours. The solid precipitate settled quickly from solution.

The solid precipitate,

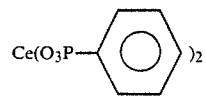

was separated from the supernatant liquid by filtration. A precipitate so separated was washed with water. The precipitate was then dried at a temperature of about 55° C. overnight. The recovered precipitate has a light yellow color.

Elemental analysis of the recovered product provided the following results: 32.56% C; 2.52% H; and 25.3% Ce. An X-ray powder diffraction pattern showed the compound to be crystalline having an interlayer spacing of 15.5 Å.

EXAMPLE VI

Preparation of:

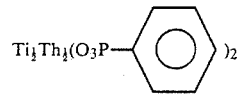

In a suitable flask 1.657 g of a 30% by weight aqueous solution of $TiOCl_2$ was mixed with 2.048 g of $Th(NO_3)_4 \cdot 4H_2O$ in about 20 ml of water. The resultant mixture was added to about a 100 ml round bottom flask containing 1.173 g of

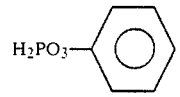

dissolved in about 20 ml of water.

Upon mixing the two solutions a precipitate of

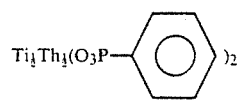

appeared. The reaction sequence was conducted under a hood using a scrubber containing sodium hydroxide solution to trap any acid fumes of hydrofluoric acid which was added in an amount of a few drops to dissolve the precipitate formed. The hydrofluoric acid was a 48% hydrofluoric acid. The reaction mixture following the addition of the hydrofluoric acid was refluxed to assist in layering.

Following refluxing, the reaction mixture was filtered. The solid

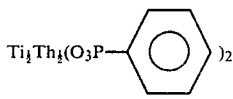

separated was washed with water, followed by an acetone wash. The solid was then dried for about one hour at about 85° C. The solid recovered weighed 2.345 g.

Elemental analysis of the recoverd product provided the following results: 22.14% C; 2.34% H; 9.64% P; 5.50% Ti; and 22.1% Th. An X-ray powder diffraction pattern showed the compound to be crystalline having an interlayer of 16.0 Å.

EXAMPLE VII

Preparation of:

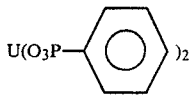

In a suitable reaction vessel, 1.292 g of

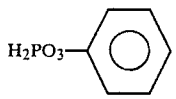

was dissolved in a sufficient amount of water to form a solution. A stoichiometric amount of $UCl_4$, 1.552 g, was dissolved in a sufficient amount of water to dissolve the $UCl_4$ and the resultant solution of $UCl_4$ was mixed with the aqueous solution of

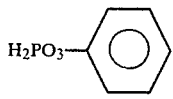

A green precipitate appeared immediately upon mixing. To the resultant mixture was added one ml of hydrochloric acid. The mixture was then heated near reflux temperatures for overnight. Within about 15 minutes of heating the mixture the green precipitate developed a gray/purple color.

Following refluxing the mixture the form precipitate was filtered and separated from the supernatant liquid. A precipitate being

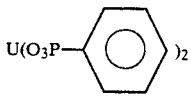

was washed with water followed by an acetone wash. The precipitate was then dried at about 100° C. for about one-half hour. The resulting dark gray/purple solid precipitate after drying weighed about 2.041 grams. The theoretical yield for the reaction would have produced 2.248 g of

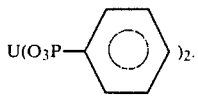

Thus providing a percentage yield of about 91 percent.

Elemental analysis of the recovered product provided the following results: 26.06% C; 1.97% H; and 41.8% U. An X-ray powder diffraction pattern showed the compound to be crystalline having an interlayer spacing of 15 Å.

EXAMPLE VIII

Preparation of: $Zr(O_3PC_6H_5)_2$

A solution of 2.990 g of $ZrOCl_2.8H_2O$ dissolved in 20 ml of deionized water was placed in a round bottom flask fitted with a reflux condenser, stirrer and heating mantle. To this was added 30 ml of an aqueous solution containing 6.040 g of phenylphosphonic acid, with stirring. A white precipitate formed very rapidly. The mixture was heated to about 90° C. and maintained at this level for two days.

After cooling to room temperature, the solid was isolated by filtration, washed with water, washed with acetone, and dried at 55° C. for one hour. The yield was 4.782 g.

The infrared absorption spectrum of this solid indicates the presence of an aromatic substituent in the compound. An X-ray diffraction pattern confirmed the expected interlayer spacing of 14.9 Å. Analysis of the solid gave the following results:

| Constituent | Calculated % | Observed % |
|---|---|---|
| Carbon | 35.70 | 37.20 |
| Hydrogen | 2.48 | 3.07 |

These data confirm the empirical formula for the product of $Zr(O_3PC_6H_5)_2$.

EXAMPLE IX

Preparation of:

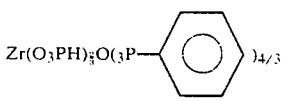

In a reaction flask was added an aqueous solution which had been formulated by dissolving 2.004 g of $ZrOCl_2.8H_2O$ in water which had been deoxygenated by bubbling in nitrogen gas therethrough. The reaction flask was then blanketed with an inert atmosphere of nitrogen and the solution was mixed with a solution containing 3.086 g of a 30% by weight $H_3PO_3$, 1.778 g phenyl phosphonic acid and one ml of hydrochloric acid. Deoxygenated water was added to bring the total volume to abut 75 ml.

The resulting mixture was heated until it started to exhibit refluxing. A solid precipitate appeared. The mixture was then divided into two equal portions. The first portion was filtered and the separated precipitate was washed with successive washes of water and acetone. This first precipitate was dried at about 80° C. The second portion of the mixture was heated and refluxed under nitrogen atmosphere for about 24 hours. Following refluxing the second portion of the mixture was filtered to separate the second precipitate from the liquid. The recovered second precipitate was washed successively with water and acetone and dried at about 80° C. for a few hours.

The first precipitate recovered from the first portion of the mixture weighed about 0.728 g, and the second precipitate recovered from the refluxed second portion weighed about 2.156 g. The total combined weight of the recovered precipitates,

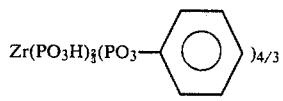

was 2.884 g.

Elemental analysis of the recovered first product provided the following results: 25.05% C and 2.06% H. An X-ray powder diffraction pattern showed the compound to be amorphous.

Elemental analysis at the recovered second product provided the following results: 27.22% C and 2.88% H. An X-ray powder diffraction pattern showed the compound to be semicrystalline having an interlayer spacing of 15.8 Å.

EXAMPLE X

Preparation of:

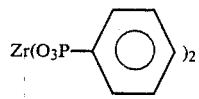

A solution of 2.990 g of $ZrOCl_2 \cdot 8H_2O$ dissolved in 20 ml of deionized water was placed in a round-bottom flask fitted with a reflux condenser, stirrer and heating mantle. To this was added 30 ml of an aqueous solution containing 6.040 g of phenylphosphonic acid, with stirring. A white precipitate formed very rapidly. The mixture was heated to about 90° C. and maintained at this level for two days.

After cooling to room temperature, the solid was isolated by filtration, washed with water, washed with acetone, and dried at 55° C. for one hour. The yield of

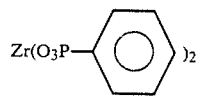

was 4.782 g.

EXAMPLE XI

An aqueous solution of organic compounds for use in sorption experiments was prepared by shaking 25 ml of chloroform, 25 ml of toluene and 25 ml of hexane in a separatory funnel with 100 ml of deionized water for ten minutes. After settling for five minutes, the aqueous layer was separated and stored in a stoppered flask.

A gas chromatographic analysis of the aqueous solution yielded peaks for ethanol (a stabilizer present in the chloroform reagent used), chloroform and water. The ratio of chloroform peak area to ethanol peak area was determined for two samples at 15 minute intervals prior to beginning the sorption experiment.

A 3.060 g portion of zirconium phenylphosphonate was added to the aqueous solution, the stopper replaced, and the mixture agitated briefly. After 15 minutes, a sample was agitated, then allowed to settle for about five minutes prior to obtaining each of the remaining samples in the experiment.

Ethanol was not extracted from the solution in a significant amount. However, more than 50 percent of the chloroform was extracted by the $Zr(O_3PC_6H_5)_2$ compound. This indicates the utility as a selective sorbent which removes specific contaminants from solutions, while leaving other dissolved materials in solution.

EXAMPLE XII

An aqueous solution of organic compounds for use in absorption experiments was prepared by shaking 25 ml of chloroform, 25 ml of benzene and 25 ml of n-hexanol in a separatory funnel with 100 ml of deionized water. After settling, the aqueous layer was separated and placed into a 125 ml Erlenmeyer flask containing a stirring bar and the flask was sealed. This solution was stirred continuously during sampling and experimentation. First, some small samples were taken about every 15 minutes to establish a baseline concentration of each organic in the water.

A 2.442 g sample of ground

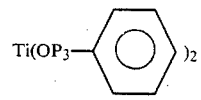

was added quickly to the solution. This mixture was shaken for a minute to prevent the solid from floating on the water. Aqueous samples were taken after allowing the solid to partially settle in order to obtain a clear solution for gas chromatographic analysis.

On gas chromatograph testing, a slow but continuous drop of organics and then a sudden drop in concentration of all three (n-hexanol, benzene and chloroform) was shown when the

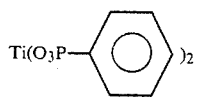

was added to the system. A leveling off occurred after the initial rapid extraction and at time infinity.

A plot of the area of an ethanol peak from gas chromatography data shows a fairly constant concentration of the ethanol throughout the whole experiment indicating it is a reliable internal reference peak. Ethanol seemed more soluble in water over the solid. The ethanol came from the chloroform used in the experiment. The chloroform contained about one percent ethanol stabilizer. The

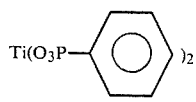

had an affinity to absorb the organic compounds. The weight distribution coefficient ($K_{wt}$) and the molar distribution coefficient ($K_m$) for the n-hexanol, chloroform and benzene were determined to be as follows for the

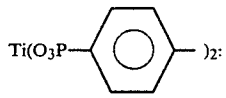:

| | | | |
|---|---|---|---|
| N—hexanol | $K_{wt}$ 28.22 | $K_m$ | 564.2 |
| Chloroform | 20.26 | | 405.1 |
| Benzene | 53.19 | | 1063.5 |

These results indicate the utility of the compound as a selective solvent which can remove specific contaminants from solutions while leaving other dissolved materials in the solution.

Other metal$^{+4}$ ions which are analogous to $Zr^{+4}$ in the process to make phosphate and phosphonate analogs, are metals with approximately the same ionic radius as $Zr^{+4}$ (0.8 Å), for example,

| | | | |
|---|---|---|---|
| $Zr^{+4}$ 0.80Å | $Te^{+4}$ 0.81 | $Pr^{+4}$ 0.94 | $Mn^{+4}$ 0.5 |
| $W^{+4}$ 0.66 | $Sn^{+4}$ 0.71 | $Pb^{+4}$ 0.92 | $Ir^{+4}$ 0.66 |
| $U^{+4}$ 0.89 | $Si^{+4}$ 0.41 | $Os^{+4}$ 0.67 | $Hf^{+4}$ 0.81 |
| $Ti^{+4}$ 0.68 | $Ru^{+4}$ 0.65 | $Nb^{+4}$ 0.67 | $Ge^{+4}$ 0.53 |
| $Th^{+4}$ 0.95 | $Pu^{+4}$ 0.86 | $Mo^{+4}$ 0.68 | $Ce^{+4}$ 1.01 |

The thio analogs of the phosphonates and phosphates can also be made by this process. The larger, more readily redoxable elements can lead to semiconducting, photoactive supports. All of the above noted solid, layered compounds can be useful as a chromatographic solid phase, adsorbants ion-exchange and hosts or carriers for controlled release of active substances.

In the preparation of anchorable Layered Compounds, a general approach to zirconium phosphate and the other zirconium compositions described herein and in the applications incorporated herein involve the following concepts:

(1) Tetrahedral anions with 3-metal coordinating groups and one interlayer group desirable

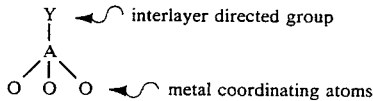

(2) Charge on anion should be −1, −2, −3 (charge on metal ion therefore should be +2, +4, +6 for M[O$_3$AY]$_2$ stoichiometry needed for sandwiching and bridging configuration)

(i) for −1 charge, conjugate acid of anion is 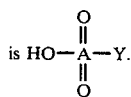

"A" can be S (or Se, Cr, Mo, W, etc., (+6 forming elements)

(ii) for −2 charge, conjugate acid of anion

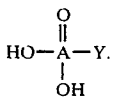

"A" can be P, As, Sb, V, Nb, Ta, etc., (+5 forming elements)

(iii) for −3 charge, conjugate acid of anion is

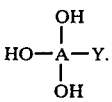

"A" can be Si, Ge, Ti, Zr, Sn, Pb (+4 forming elements).

Some exemplary salts which meet these criteria are listed below.

M[O$_3$A—Y]$_2$: Examples of compounds of structure which can form layered host structures analogous to zirconium phosphate and the phosphorous or arsenic containing compounds of the applications incorporated herein:

(1) [O$_3$A—Y]$^{-1}$ A=S, for example, Y=NH$_2$ (conjugate acid is sulfamic acid), M+ =$Cu^{+2}$, $Zn^{+2}$, $Fe^{+2}$, alkaline earths

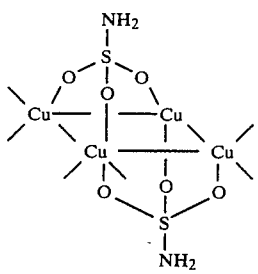

(2) [O$_3$A—Y]$^{-2}$—Zirconium phosphate prototypes (A=P, As, Sb, etc.)

(3) [O$_3$A—Y]$^{-3}$—A=Si, for example, Y=OCH$_2$CN, M=$Mo^{+6}$

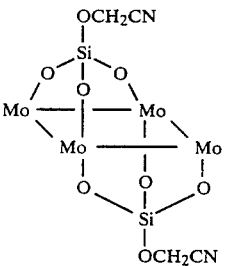

In all cases, metal ion is in octahedral sphere (could be trigonal prism).

Although the structure of these solid phases is polymeric in nature, it is convention in solid inorganic nomenclature to refer to them by their monomeric units.

What is claimed is:

1. Solid inorganic polymers derived from organo group-containing phosphorous or phosphoric acids, in which the organo group is selected from the group consisting of alicyclics, aromatics and heterocyclics wherein, three oxygens bonded to phosphorus are structurally linked to one or more tetravalent metals selected from the group consisting of titanium, zirconium, cerium, hafnium, lead, thorium and uranium, and wherein the molar ratio of phosphorus to tetravalent metal is about 2 to 1.

2. Solid inorganic polymers, as in claim 1, providing pendant organo groups, and which contain structural units of the formula:

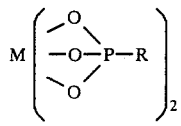

wherein R is an organo group selected from the group consisting of alicyclics, aromatics and heterocyclics wherein, three oxygens bonded to phosphorus are structurally linked to one or more tetravalent metals, M, selected from the group consisting of titanium, zirconium, cerium, hafnium, lead, thorium and uranium, and wherein the molar ratio of phosphorus to tetravalent metal is about 2 to 1.

3. Solid inorganic polymers, as in claim 1, which are phosphonates, providing pendant organo groups, and which contain structural units of the formula:

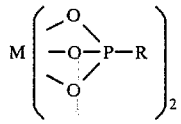

wherein R is an organo group which is bonded to phosphorus through carbon and selected from the group consisting of alicyclics, aromatics and heterocyclics wherein, three oxygens bonded to phosphorus are structurally linked to one or more tetravalent metals, M, selected from the group consisting of titanium, zirconium, cerium, hafnium, lead, thorium and uranium, and wherein the molar ratio of phosphorus to tetravalent metal is about 2 to 1.

4. Solid inorganic polymers, as in claim 3, in which R contains up to about 26 carbon atoms.

5. Solid inorganic polymers, as in claim 1, which are phosphates, providing pendant organo groups, and which contain structural units of the formula:

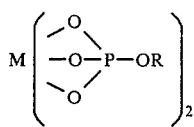

wherein R is an organo group which is bonded to phosphorus through an oxygen-carbon bond and selected from the group consisting of alicyclics, aromatics and heterocyclics wherein, three oxygens bonded to phosphorus are structurally linked to one or more tetravalent metals, M, selected from the group consisting of titanium, zirconium, cerium, hafnium, lead, thorium and uranium, and wherein the molar ratio of phosphorus to tetravalent metal is about 2 to 1.

6. Solid inorganic polymers, as in claim 5, in which R contains up to about 26 carbon atoms.

7. The composition of claim 5, which is a solid inorganic polymer of zirconium bis(p-nitrophenylphosphate).

8. The composition of claim 3, which is a solid inorganic polymer of thorium bis(phenylphosphonate).

9. The composition of claim 3, which is a solid inorganic polymer of titanium bis(phenylphosphonate).

10. The composition of claim 5, which is a solid inorganic polymer of thorium bis(p-nitrophenylphosphate).

11. The composition of claim 3, which is a solid inorganic polymer of cerium bis(phenylphosphonate).

12. The composition of claim 3, which is a solid inorganic polymer having the empirical formula $Ti_{1/2}Th_{1/2}(O_3PC_6H_5)_2$.

13. The composition of claim 3, which is a solid inorganic polymer of uranium bis(phenylphosphonate).

14. Solid inorganic polymer derived from organo group-containing phosphorous or phosphoric acids, in which the organo group is selected from the group consisting of alicyclics, aromatics and heterocyclics wherein, three oxygens bonded to phosphorus are structurally linked to one or more tetravalent zirconium atoms, and wherein the molar ratio of phosphorus to zirconium metal is about 2 to 1.

* * * * *